United States Patent
Undheim (10) Patent No.: US 12,038,392 B2
(45) Date of Patent: Jul. 16, 2024

(54) SYSTEM FOR DETECTION OF DRIFT OF THE WATER VOLUME FRACTION IN A FLOW

(71) Applicant: Roxar Flow Measurement AS, Stavanger (NO)

(72) Inventor: Erik Undheim, Bryne (NO)

(73) Assignee: Roxar Flow Measurement AS, Stavanger (NO)

( * ) Notice: Subject to any disclaimer, the term of this patent is extended or adjusted under 35 U.S.C. 154(b) by 437 days.

(21) Appl. No.: 17/299,381

(22) PCT Filed: Feb. 13, 2020

(86) PCT No.: PCT/EP2020/053674
§ 371 (c)(1),
(2) Date: Jun. 3, 2021

(87) PCT Pub. No.: WO2020/165299
PCT Pub. Date: Aug. 20, 2020

(65) Prior Publication Data
US 2022/0026376 A1     Jan. 27, 2022

(30) Foreign Application Priority Data
Feb. 15, 2019    (NO) .................................. 20190211

(51) Int. Cl.
| | | |
|---|---|---|
| *G01N 22/04* | (2006.01) | |
| *G01N 27/22* | (2006.01) | |
| *G01N 33/28* | (2006.01) | |

(52) U.S. Cl.
CPC ........... *G01N 22/04* (2013.01); *G01N 27/223* (2013.01); *G01N 33/2823* (2013.01); *G01N 33/2847* (2013.01)

(58) Field of Classification Search
CPC .. G01N 27/223; G01N 22/04; G01N 33/2847; G01N 33/2823; G01N 33/28
See application file for complete search history.

(56) References Cited

U.S. PATENT DOCUMENTS

| | | | | |
|---|---|---|---|---|
| 5,576,974 A | * | 11/1996 | Marrelli .................. | G01N 22/04 |
| | | | | 702/179 |
| 2003/0011386 A1 | * | 1/2003 | Xie ..................... | G01N 33/2823 |
| | | | | 324/694 |

(Continued)

FOREIGN PATENT DOCUMENTS

| | | | | |
|---|---|---|---|---|
| GB | 2221042 A | | 1/1990 | |
| GB | 2513678 A | * | 11/2014 | ............. E21B 47/10 |

OTHER PUBLICATIONS

Pagels, Marcel; International Search Report; PCT/EP2020/053674; dated Jun. 25, 2020; 3 pages.

*Primary Examiner* — Eman A Alkafawi
*Assistant Examiner* — Suresh K Rajaputra
(74) *Attorney, Agent, or Firm* — Bradley Arant Boult Cummings LLP (57) ABSTRACT

The present invention relates to a system for measuring the water volume fraction (WVF) of a mixed fluid flow in a pipe, especially wet and dry gas hydrocarbon fluid flows, the system comprising a measuring unit for measuring the dielectric permittivity of said fluid mixture, a computing unit for calculating and storing both the WVF, based on the absolute level of the dielectric permittivity, and the statistical variation of the dielectric permittivity of said fluid mixture over a predetermined period of time. The system also including an analysis unit for detecting drift in the measured WVF by comparing and analyzing the development of the WVF versus the statistical variation of the permittivity over said time period, and based on detected drift to determine whether an apparent change in the WVF is reflected in a (Continued)

corresponding change in the statistical variation of the permittivity, and, based on said comparison, determining if the drift is caused by a real change in the WVF.

20 Claims, 8 Drawing Sheets

(56) References Cited

U.S. PATENT DOCUMENTS

| | | | |
|---|---|---|---|
| 2007/0038399 A1* | 2/2007 | Scott | G01N 33/2847 |
| | | | 702/100 |
| 2009/0088985 A1* | 4/2009 | Wee | G01F 1/66 |
| | | | 702/30 |
| 2010/0145636 A1 | 6/2010 | Nyfors | |
| 2011/0290035 A1 | 12/2011 | Wee et al. | |
| 2011/0301877 A1* | 12/2011 | Wee | G01F 1/74 |
| | | | 702/47 |
| 2013/0327154 A1 | 12/2013 | Xie et al. | |
| 2015/0160147 A1* | 6/2015 | De Paepe | F28F 27/02 |
| | | | 73/19.01 |
| 2015/0346017 A1* | 12/2015 | LePort | G01F 23/2921 |
| | | | 73/152.24 |
| 2016/0202231 A1 | 7/2016 | Black et al. | |

\* cited by examiner

FIG. 9

SYSTEM FOR DETECTION OF DRIFT OF THE WATER VOLUME FRACTION IN A FLOW

This invention relates to a system for monitoring the long-term trend of the water volume fraction (WVF) in a hydrocarbon fluid flow, predominantly where one of the hydrocarbon phases is dominating the flow, either continuously or in reoccurring and detectable periods of time.

Many wet gas fields operate with a WVF close to 0%, typically in the range of 0.005-0.3% prior to formation water break through. Permittivity measurement is the dominating sensor principle for WVF measurement in such conditions because of its sensitivity to small amounts of water. The common way of measuring the WVF in wet gas streams— with a permittivity-based sensor—is to use the measured absolute level of the permittivity of the mixture, hereafter referred to as mixture permittivity, and use some form of mixing equation to solve out the fraction of water in the mixture, e.g. the Bruggeman mixing Equation 2 in [Bruggeman, Annalen Der Physik 24 (1935) 636-664]. Another example of permittivity measurements fluid flows to calculate the water content in a fluid is discussed in U.S. Patent Application Publication No. 2016/0202231-A1.

The high permittivity contrast between water and hydrocarbons, both in gas and liquid state, makes mixture permittivity sensors a preferred option for detecting and measuring water content in hydrocarbon flows: Water has a permittivity>70, depending on salinity and temperature; oil has a permittivity of typically 1.8-2.5, strongly correlated to the oil density; gas typically has a permittivity less than 1.5, strongly correlated to the gas density and composition. In wet gas streams, extremely sensitive mixture permittivity measurement techniques are required to sense changes in WVF down to ppm levels, e.g. microwave resonators. The mixture permittivity is totally dominated by the hydrocarbon permittivity, and to separate the permittivity contribution of the hydrocarbons from ppm levels of water requires extreme precision is also required from the hydrocarbon permittivity models. A minor change in the hydrocarbon permittivity, from e.g. a change in pressure, temperature or hydrocarbon composition, causes a change in mixture permittivity that must be compensated for to calculate the correct WVF. And even if perfect hydrocarbon permittivity models and mixing equations existed, significant uncertainties are related to the hydrocarbon composition itself, the temperature and pressure measurement, as well as other sources that could affect a mixture permittivity measurement, e.g. build-up of layers such as scale and wax or long term changes to the measurement cavity from erosion and corrosion and electronics drift. Some form of drift in the measured WVF over a longer period of time is unavoidable when the absolute permittivity of the mixture is the basis of the calculation.

It is an object of the present invention to provide a solution for classifying whether a long-term apparent trend in the WVF is an actual change in the WVF or instead caused by various forms of drift, e.g. imperfect compensation for long term changes in the hydrocarbon permittivity, measurement cavity changes from erosion or corrosion, layer build-up of scale, wax or other type of layers, electronics drift, and in addition to be able to auto-compensate for the detected drift.

In a hydrocarbon flow including water there are natural variations in the flow that are reflected in the variation of the measured mixture permittivity; tunder many flow conditions the WVF is totally dominating the permittivity variation to such an extent that an actual change in WVF can always be verified by correlating change in the permittivity variation. The present invention is based on using the long-term trending of the statistical variation of the permittivity of the mixture (hereafter referred to as permittivity variation), constituted by a gas or oil dominated hydrocarbon fluid flow including content, in combination with the long-term trending of the measured WVF to improve the accuracy of the measured WVF and make sure no form of drift is affecting the measurement. When the hydrocarbon fluid flow is dominated by either gas or oil, hence a low mix permittivity, what affects the permittivity variation is totally dominated by the amount of water present. Longer term changes, or static permanent changes, to the mix permittivity do not affect the permittivity variation, thus making it possible to separate various forms of long-term drift, hydrocarbon permittivity model inaccuracies and static changes to the mix permittivity from an actual WVF change.

For the majority of conventional wet gas applications, the flow composition can be virtually unchanged (steady state) for several years until formation water break-through or other significant dynamical changes to the composition. The total flow rate, pressure and temperature are typically regulated to optimize the production, but the WVF remains stable in this period since it is dominated by condensed water from a gas saturated with water vapour leaving the reservoir. In this period, it is critical to measure the water volume fraction with the highest precision possible since the amounts of water could be close to 0%; it is also the period where the measurement is most susceptible to any form of drift in the measurements, as a small absolute error constitutes a large relative error. Any form of changes to the mixture permittivity caused by e.g. changes in the pressure, temperature or flow velocity, must be perfectly compensated for to derive the correct WVF, which in practice is highly challenging with the method of using the mixture permittivity measurement as the basis. It is the object of the present invention to make the water volume fraction measurement free for any form of drift in these steady-state periods prior to formation water break-through to make sure that formation water break-through is detected with as high precision as possible as early as possible.

Some applications based on using the statistical variation of the permittivity are known from before. They are related to permittivity variation techniques for measuring the composition of a multiphase stream of gas, oil and water, typically aims to calculate the fraction or rate of one or more of the constituents directly by various specific methods, e.g. U.S. Patent Application Publication No. 2011/0290035-A1, U.S. Pat. No. 5,576,974 and GB-2221042-A.

U.S. Patent Application Publication No. 2011/0290035-A1 describes a specific method to improve the liquid fraction, WLR and flow rates in wet gas flow, based on correcting the water fraction derived from the measured mixture permittivity and mixture density by using the permittivity variation and an empirically derived curve. The challenge with this method is that it relies on a close to perfect mix density measurement and an empirical calibration curve. Gamma-based density sensors are known for both significant drift over time and has a generally too high density uncertainty to discriminate between water and oil in wet gas conditions. The density contrast between water and oil is too small (~1000 kg/m^3 for water and ~750 kg/m^3 for oil) to give a robust resolution to various water-to-liquid ratios over time when the liquid volume fraction is in the 0-2% range.

U.S. Pat. No. 5,576,974 describes various specific methods and equations to derive the gas fraction directly based on the permittivity variation of various permittivity related signals and empirical factors, and from the gas fraction correct the water fraction in predominantly low gas water cut monitors.

GB-2221042-A describes a more general method of mapping electric output signals from various detectors, both absolute value and standard deviation, and map them to flow rates with empirically derived calibration maps.

All the solutions described above calculates one or more of the constituents of the flow directly with the level of one or more statistical parameters as a key input to the equation. The general challenge with statistical methods for direct measurements is that they rely heavily on empirically derived models only valid for dedicated electronics, sensor type, sensor size, sensor position, upstream piping arrangement etc.; it is challenging to translate statistical parameters into universal parameters that can go into established equations based on physics. In addition, for hydrocarbon flow including water, the range of the methods is limited from ambiguity for certain combination of fluids, and the time it takes to build up a statistically representative parameter is typically longer than mixture permittivity methods.

The present innovation combines the advantages of both methods for deriving the WVF in gas or oil dominated hydrocarbon flow. By using the long-term trend of the permittivity variation to detect and correct drift in the derived WVF, based on the mixture permittivity method, one removes the challenge with various forms of drift related to the absolute level of the mixture permittivity and make it possible to calculate the WVF with universal and well-established equations based on physics at the same time. There is no need for meter and installation specific empirical models for the relationship between statistical variation parameters and the flow composition, which is a general challenge with known statistical methods; it is the pattern of the permittivity variation trend itself which is the critical input to this method, and this pattern is independent of the meter design and installation. The present innovation extracts the critical information from the permittivity variation, for drift-free WVF measurement, without the disadvantages of known statistical methods. From evaluating the permittivity variation trend, it is possible to characterize the source of the drift, calculate the appropriate corrections, and give feedback to the user about the type of drift that has been detected and the corrections made. This is all in line with a key trend in the multiphase and wet gas meter industry: to get rid of the dominating black box strategy where various intangible empirical corrections are the basis of the measurement outputs.

It is also an object of the present invention to make it possible to measure the WVF based on the mixture permittivity, with required industry accuracy, in the whole gas, oil and water fraction range, without the need for switching between various modes depending on the gas fraction. The objects of the present invention are obtained according to a system as described above and characterized as specified in the accompanying claims.

It is further an object of the invention to make the flow meter able to detect various forms of drift and report to the user.

It is further an object of the invention to characterize the source of the drift.

It is further an object of the invention to detect and correct inaccurate hydrocarbon permittivity model coefficients causing WVF drift with changing pressure or temperature.

It is further an object of the invention to reduce or remove the need for regular maintenance of installed flow meters, including regular calibration.

It is further an object of the invention to provide more accurate self-diagnostics as well as a user report.

It is further an object of the invention to make the flow meter able to self-compensate for various forms of drift.

The present invention overcomes the issues mentioned above by using the long-term trend of the statistical variation, instead of aiming to calculate one or more of the composition constituents directly based on the level or spectrum of the permittivity variation that may change from said factors. The long-term trend of the statistical variation may be monitored over days, months and years, together with the corresponding trend of the WVF based on the mixture permittivity, and the correlation between these two trends is used to determine possible drift in the WVF. The drift may then be characterized by various pattern recognition techniques by correlating the WVF drift trend against other sensor inputs related to flow conditions, e.g. pressure and temperature. Based on the characterization, the appropriate correction can be calculated and applied. Using the absolute measured level of the mixture permittivity to calculate the WVF has no range limitations, i.e. it can be used in the whole water-to-liquid and gas volume fraction range, but is in gas and oil dominating flow conditions sensitive to even small uncertainties related to the permittivity of the dominating hydrocarbon phase (gas or oil). It is the purpose of the invention to provide more accurate and drift-free measurements with the mixture permittivity based WVF measurement method in oil and predominantly gas dominated flow conditions.

The statistical permittivity variation trend may be based on either standard deviation, variance, skewness or higher order statistical properties, as well as frequency spectrum information, represented by one or more parameters. The parameters are calculated based on a statistically representative moving time series of data, typically in the range of seconds and minutes. The same moving time series of data is typically used as the basis for the absolute level of the mixture permittivity, used for calculating the WVF. The statistical variation of the real and imaginary part of the mixture permittivity may be measured using any type of permittivity sensor technology, e.g. microwave measurements using the resonance frequency and Q-factor, microwave transmission technologies tracking the amplitude and phase shift caused by the flow or capacitive or inductive technologies measuring the low frequency impedance of the flow.

As an exemplification, the present invention may use a microwave resonator as basis for a full cross-sectional measurement of the mixture permittivity, where the mixture permittivity is derived from the resonance frequency and Q-factor of the resonance peak. The following equations may then be involved in an embodiment of the invention:

Equation 1, absolute mixture permittivity measurement with a resonator, where $\varepsilon_{mix}$=mixture permittivity, $f_{vacuum}$=resonance frequency in vacuum and $f_{measured}$=measured resonance frequency:

$$\varepsilon_{mix} = \left(\frac{f_{vacuum}}{f_{measured}}\right)^2$$

Equation 2, WVF based on Bruggeman mixing equation—gas or oil dominated flow, where $\varepsilon_{water}$=water permittivity and $\varepsilon_{hydrocarbons}$=permittivity of the hydrocarbons in the mix:

$$WVF = 1 - \frac{\varepsilon_{water} - \varepsilon_{mix}}{\varepsilon_{water} - \varepsilon_{hydrocarbons}} * \left(\frac{\varepsilon_{hydrocarbons}}{\varepsilon_{mix}}\right)^{\frac{1}{3}}$$

Equation 3, Hydrocarbon permittivity, where $\varepsilon_{gas}$=gas permittivity, $\varepsilon_{oil}$=oil permittivity and CGR=condensate or oil to gas ratio:

$\varepsilon_{hydrocarbon}$=function($\varepsilon_{gas},\varepsilon_{oil}$,CGR)

Equation 4, Gas permittivity, typically a function of the pressure, temperature and the hydrocarbon composition:

$\varepsilon_{gas}$=function(pressure,temperature,hydrocarbon composition)

Equation 5, Oil permittivity, typically a function of the pressure (P), temperature (T), the hydrocarbon composition and the frequency:

$\varepsilon_{oil}$=function(P,T,hydrocarbon composition,resonance frequency)

Equation 6, CGR=condensate or oil to gas ratio, typically a function of the pressure (P), temperature (T) and the hydrocarbon composition:

CGR=function(P,T,hydrocarbon composition)

Equation 7, Permittivity variation parameter of the mixture based on the standard deviation calculated for a statistically representative time series or sample series typically in the range of seconds or minutes:

$\varepsilon_{mix\text{-}variation\text{-}std}$=std(moving time series of $\varepsilon_{mix}$)

Equation 8, Permittivity variation parameter of the mixture based on the skewness calculated for a statistically representative time series or sample series typically in the range of seconds or minutes:

$\varepsilon_{mix\text{-}variation\text{-}skew}$=skewness(moving time series $\varepsilon_{mix}$)

Equation 9, Permittivity variation parameter of the mixture based on the FFT (Fast Fourier Transformation) and the variation in a certain frequency range, from frequency 1, f1, to frequency 2, f2, calculated for a statistically representative time series or sample series typically in the range of seconds or minutes:

$$\varepsilon_{mix\text{-}variation\text{-}fft} = \sum_{f1}^{f2} FFT(\text{moving time series } \varepsilon_{mix})$$

The present invention will be described more in detail with reference to the accompanying drawings, illustrating the invention by way of examples.

Figure 1:
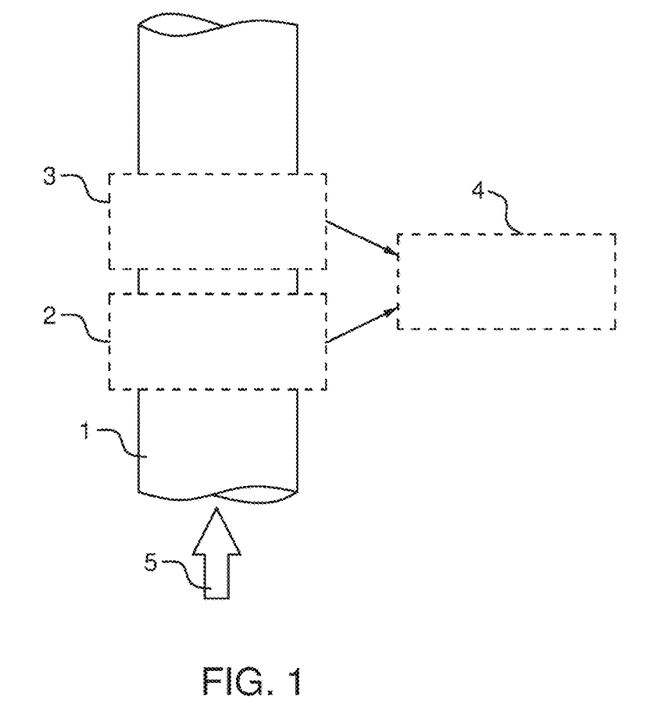
FIG. 1 illustrates a measuring system for performing the measurements according to the invention.

As is illustrated in FIG. 1, the measurement system consists of a pipe 1 with a mixture permittivity sensor 2, other application dependent multiphase instrumentation and sensors 3, and a processing unit 4. The composition calculations are performed in 4, based on the mixture permittivity and the multiphase instrumentation inputs; this is where the invention comes in as an additional feature, to improve long-term accuracy and robustness of the water volume fraction measurement by detecting and compensating for various form of WVF measurement drift. The application dependent multiphase instrumentation and sensors typically include sensors for measuring the pressure, temperature, density and the differential pressure over a flow restriction for the calculation of the mass flow rate.

Figure 2:
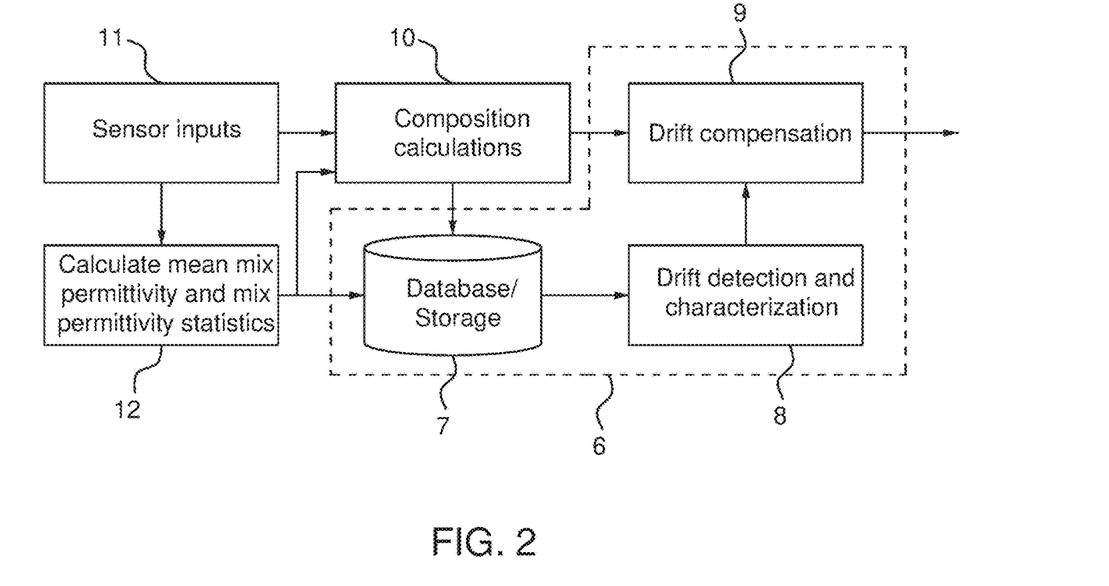
FIG. 2 shows the composition calculation with drift detection and compensation.

FIG. 2 illustrates the sequence diagram of the composition calculation part of processing unit 4 in FIG. 1, where the parts comprised by the invention are placed within the stippled area 6. Composition calculations 10 are performed based on the direct sensor inputs 11 from the sensors 2,3 and the calculated mixture permittivity. The WVF values derived from the absolute level of the mixture permittivity 10 are stored with time stamps in a database 7, or other types of storage, together with statistical information about the permittivity 12, the mixture permittivity and all other sensor inputs, over a predefined time period, a period that could be up to a range of years. The mixture permittivity and all other sensor inputs are required to be able to post-process the results in the period. The drift detection and characterization algorithm 8 continuously evaluates the trend of the historical WVF values and permittivity variation statistics stored in the database 12 to determine whether the WVF is stable, has changed, or if some form of drift has occurred. If drift is detected, the appropriate compensation can be calculated 9, or an alarm or alert can be triggered for manual user interpretation of the drift, or both.

Figure 3:
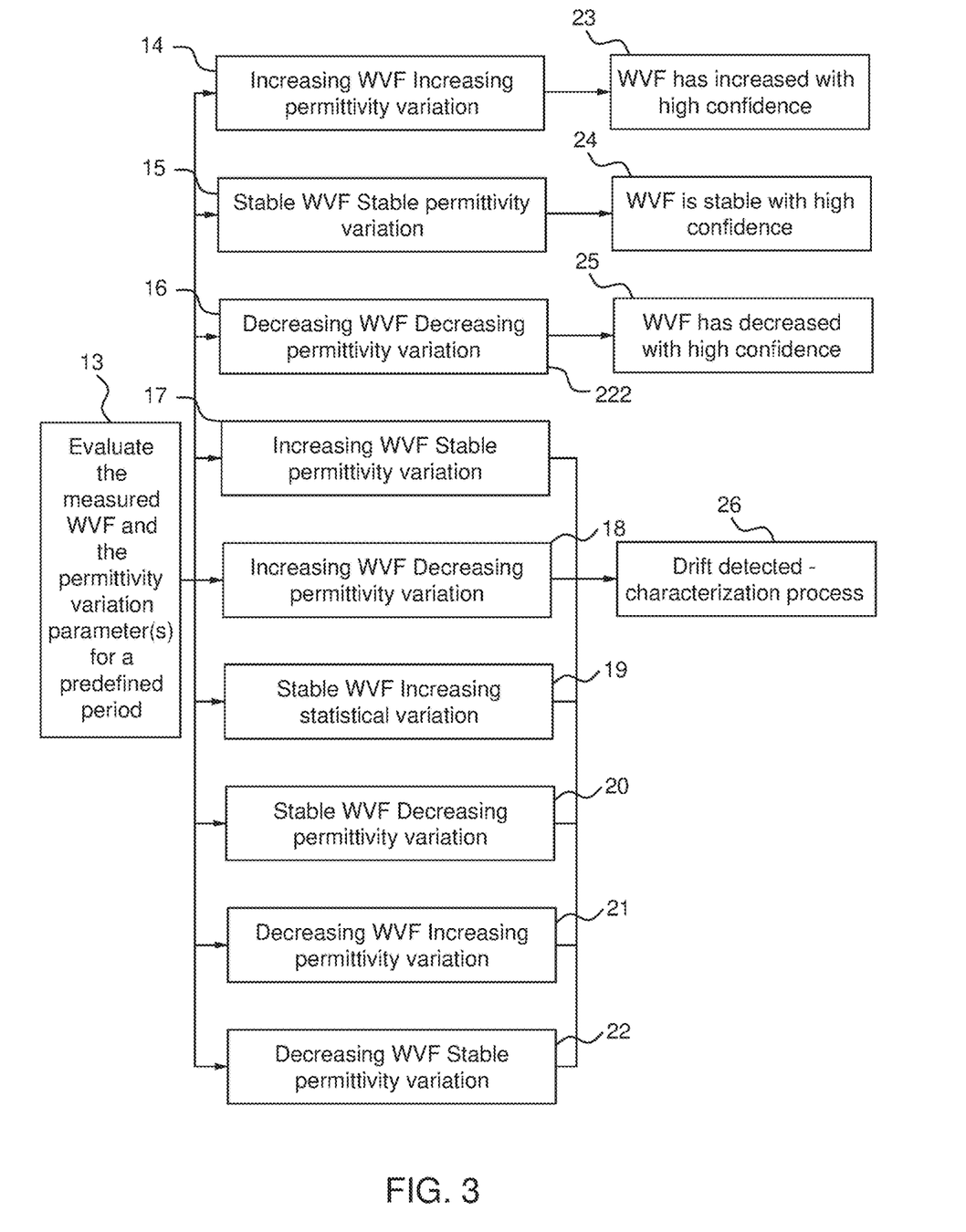
FIG. 3 shows a flow chart for the permittivity development evaluation process (Drift detection and characterization block of FIG. 2).

FIG. 3 further exemplifies the drift detection and characterization block 8 of FIG. 2, the core part of the invention. This example is typical for wet gas applications, where the effect of oil is negligible on the statistical variation. As is illustrated, the trend of the water volume fraction can always be confirmed by a corresponding and correlating trend in the statistical variation of the mixture permittivity.

In the characterization block 8 the trend of the WVF and permittivity variation is evaluated for a predefined period 13. From the top of the scheme and down this results in the following characterization:

14. Increasing WVF and increasing permittivity variation is characterized as a high confidence in that the WVF has indeed increased 23.
15. Stable WVF and stable permittivity variation is characterized as a high confidence in that the WVF is stable 24.
16. Decreasing WVF and decreasing permittivity variation is characterized as a high confidence in that the WVF has indeed decreased 25
17. Increasing WVF and stable permittivity variation is characterized as detected drift 26.
18. Increasing WVF and decreasing permittivity variation is characterized as detected drift 26.
19. Stable WVF and increasing permittivity variation is characterized as detected drift 26.
20. Stable WVF and decreasing permittivity variation is characterized as detected drift 26.
21. Decreasing WVF and increasing permittivity variation is characterized as detected drift 26.
22. Decreasing WVF and stable permittivity variation is characterized as detected drift 26.

Figure 4:
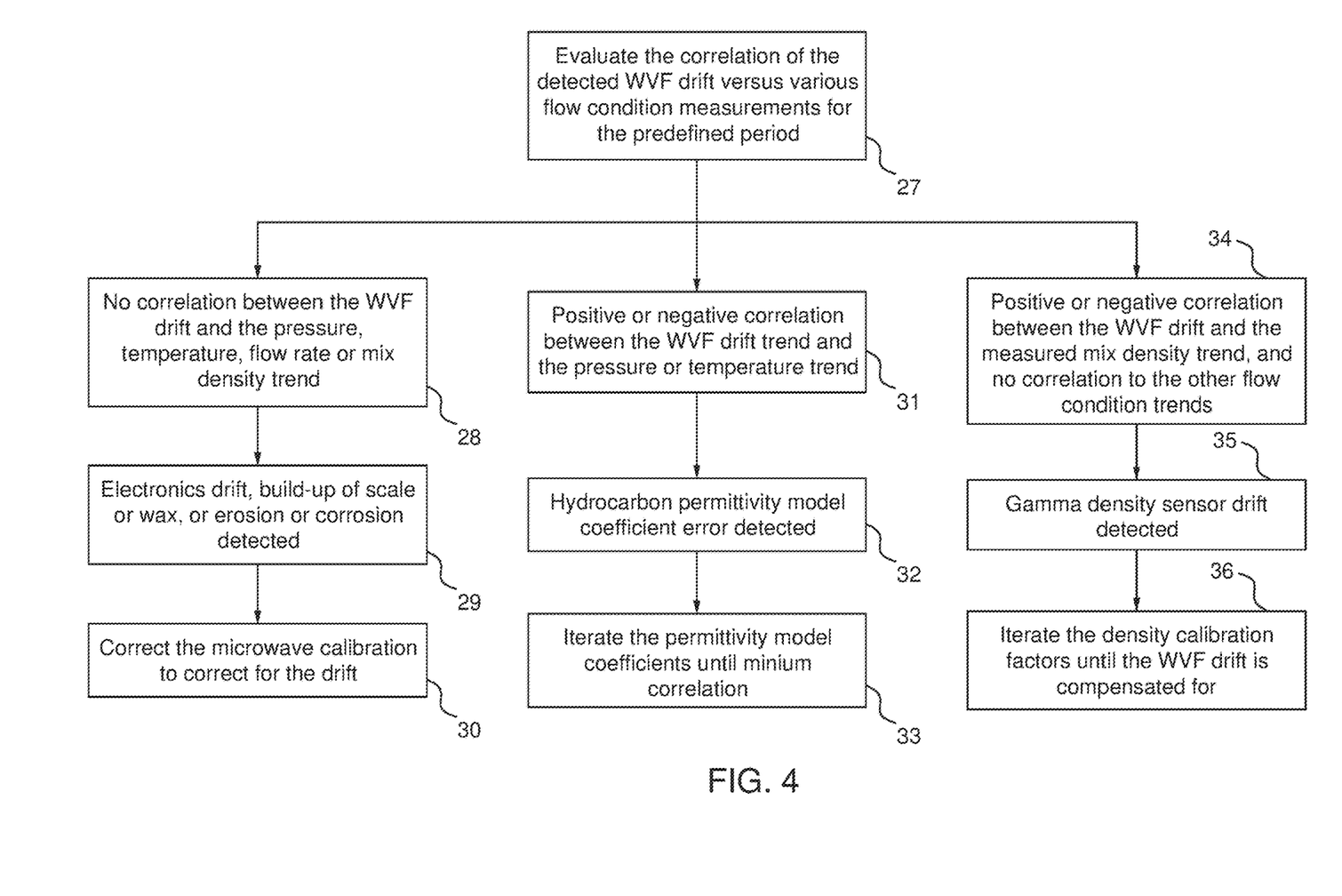
FIG. 4 shows a flow chart as an example of drift characterization and correction sequence.

FIG. 4 exemplifies the block "Drift detected—characterization" 26 in FIG. 3, where pattern recognition may be used to characterize the type of drift that has occurred, and where the correction to the drift is calculated. The sequence diagram starts with an evaluation 27 of the detected drift, and gives three examples for when the drift can be characterized by correlation to various flow condition parameters and corrected for:

28. If no correlation is found between the WVF drift versus the pressure, temperature, flow rate or mix density trend 28, the drift can be characterized as electronics drift, build-up of some type of layer, e.g. scale or wax, erosion or corrosion 29. In this case the measurement cavity or signal source has changed, and the correction may involve correcting the microwave calibration coefficients 30.
29. If a positive or negative correlation between the WVF drift trend and the pressure or temperature trend is found 31 the drift can be characterized as inaccurate hydrocarbon permittivity model coefficients 32. The coefficients can be corrected by iterating their value until the correlation is minimized for the period evaluated 33.
30. If a positive or negative correlation between the WVF drift and the measured mix density trend is found, and in the same period no correlation to the other flow condition parameters 34, the drift may be characterized as gamma density sensor drift 35. The gamma sensor may be corrected by iterating the density calibration coefficients until the WVF drift is compensated for 36.

Figure 5:
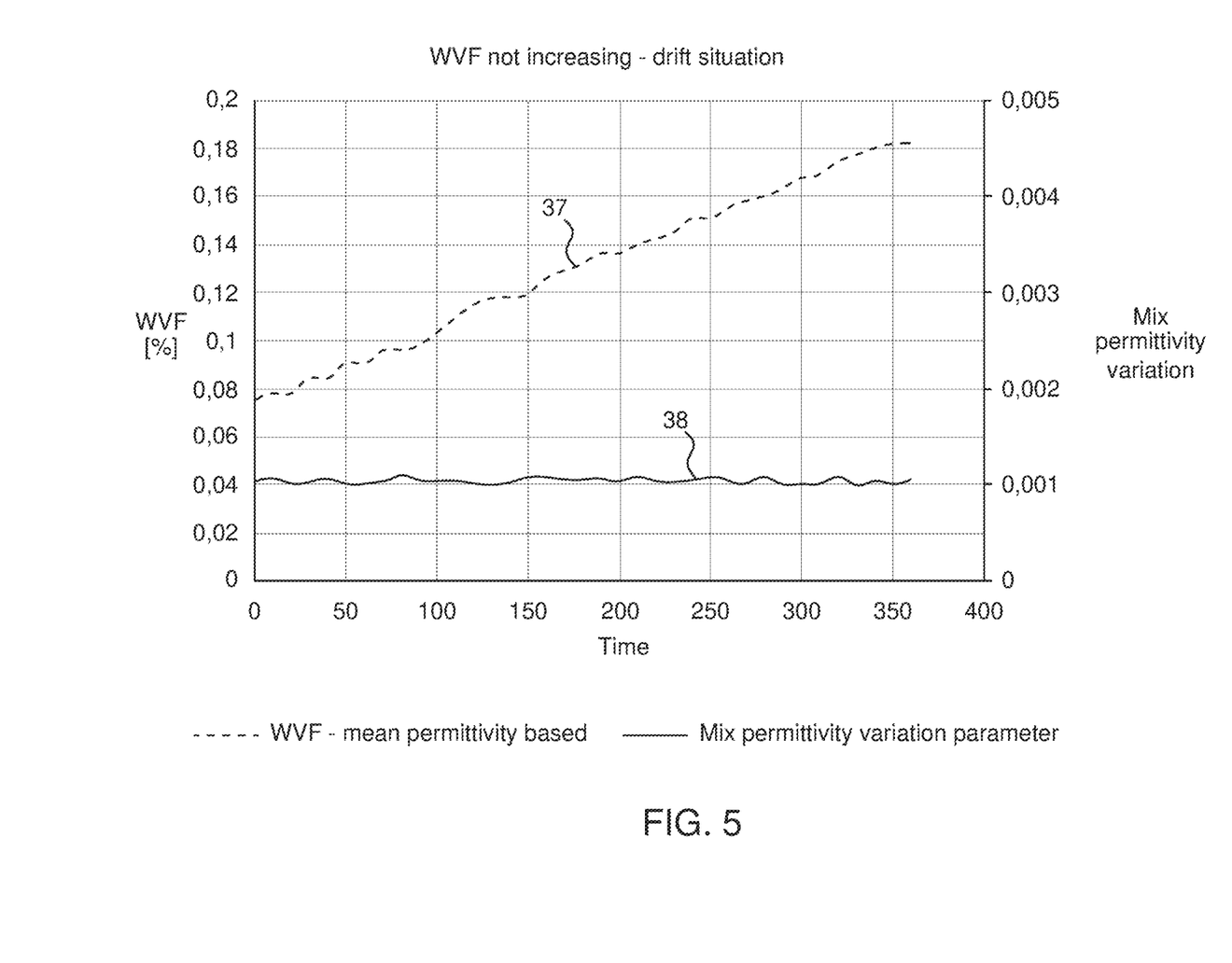
FIG. 5 shows a time series of the WVF based on mixture permittivity, and the mixture permittivity variation, for a time period where the measured WVF increases but the mixture permittivity variation parameter indicates no change; some form of drift is causing the apparent WVF increase.

FIG. 5 exemplifies a drift situation where the measured WVF 37, calculated based on the mixture permittivity, has increased over a time period without being reflected in a change in the mixture permittivity variation parameter 38. In a gas or oil dominant fluid mixture, this situation indicates that some form of drift has occurred, either related to physical changes to the measurement cavity, electronics drift, or the hydrocarbon permittivity models compensating for changing conditions.

Figure 6:
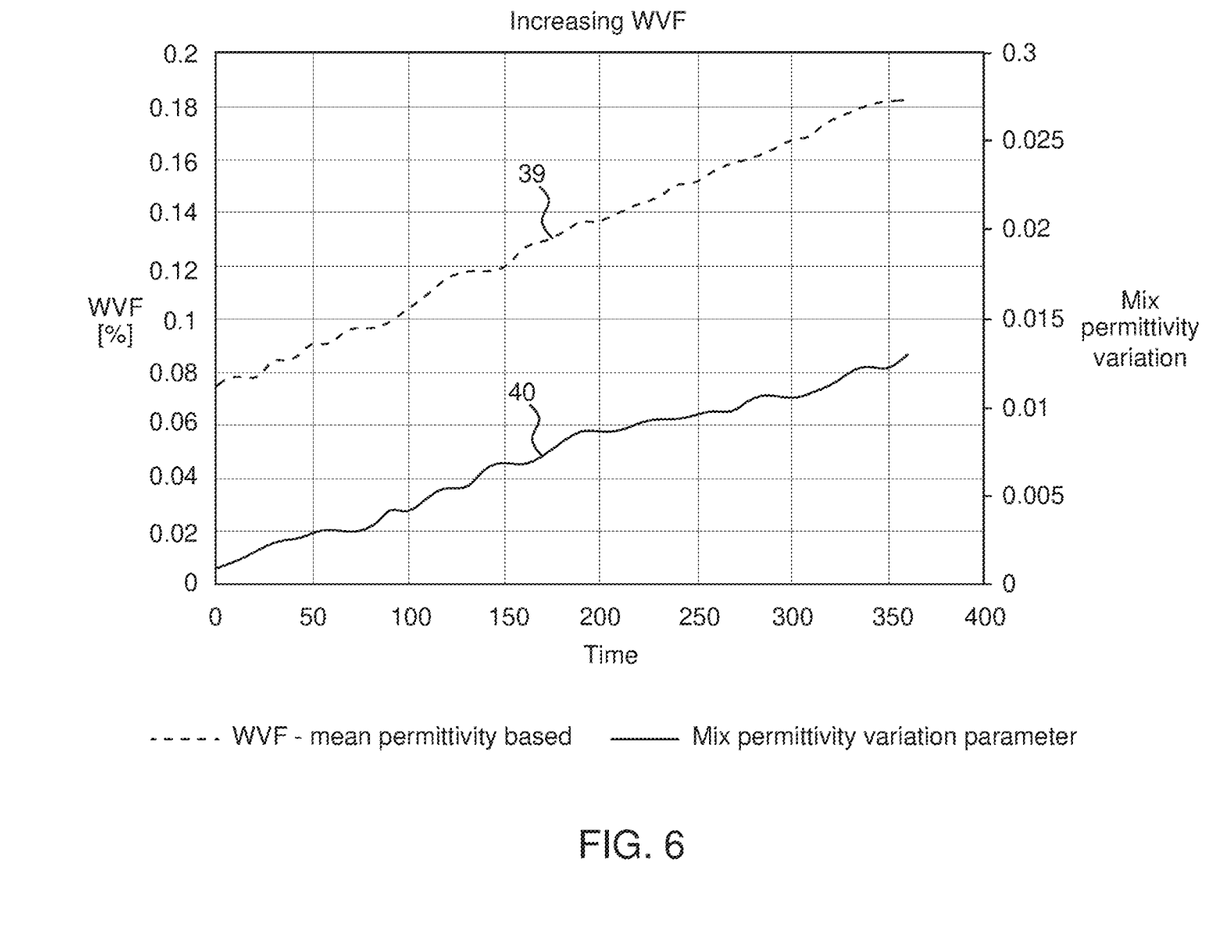
FIG. 6 shows a time series of the WVF based on mixture permittivity, and the mixture permittivity variation, for a time period where there is a real change in the WVF in high gas or oil dominant flow conditions; both values are trending in the same direction.

FIG. 6 illustrates how an actual increase in WVF affects both the measured WVF 39, based on the mixture permittivity, and the permittivity variation parameter 40, if the flow is dominated by either gas or oil. The correlating trend between the two confirms with high confidence that the water volume fraction has actually changed over the period.

Figure 7:
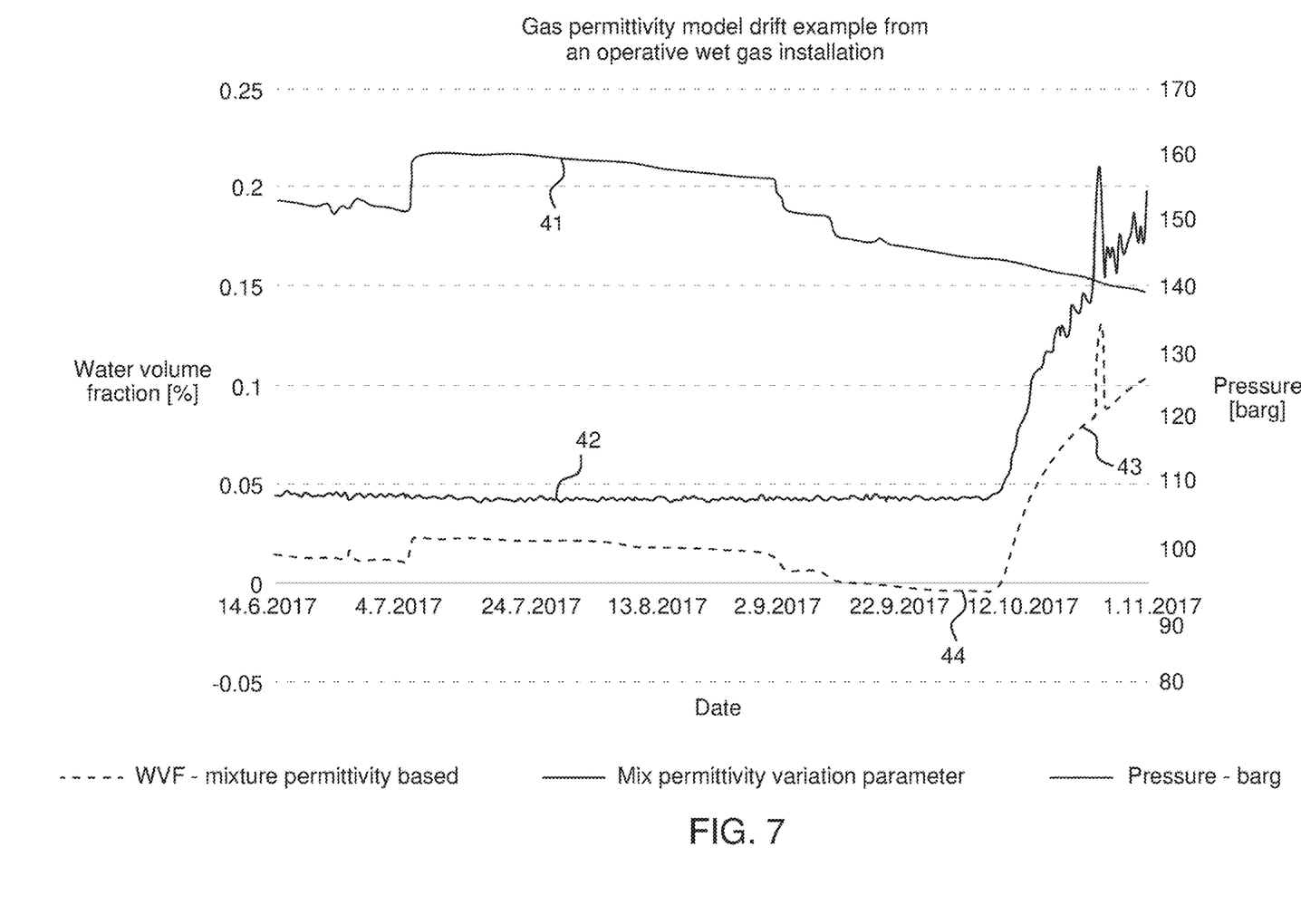
FIG. 7 shows a real field example with a subsea wetgas meter, where the change in pressure 41 affects the measured WVF 43, whilst the mixture permittivity variation parameter 42 remains stable and unaffected by the pressure changes, until water-break through around the date Dec. 10, 2017, an indication of inaccurate hydrocarbon permittivity model coefficients.

FIG. 7 is an example from an operative subsea wetgas meter measuring the WVF 43, pressure 41 and a mixture permittivity variation parameter 42, over a five-month period. As can be seen the mixture permittivity variation parameter 42 is stable at one level until the water breakthrough 44 around 12th of October, indicating stable water production. In the same period, one can see that the measured WVF 43, derived from the mixture permittivity, has a decreasing trend, closely correlated to the pattern of the decreasing pressure 41. Inaccurate gas permittivity model coefficients caused this over-compensation of the gas permittivity that occurred in this period. With the invention, by analysing a long period of stored WVF and permittivity variation data, such model inaccuracies can be detected and corrected for by the meter itself without manual human intervention and analysis, or if preferred, corrected manually, triggered by a drift detection alert or alarm from the meter.

Figure 8:
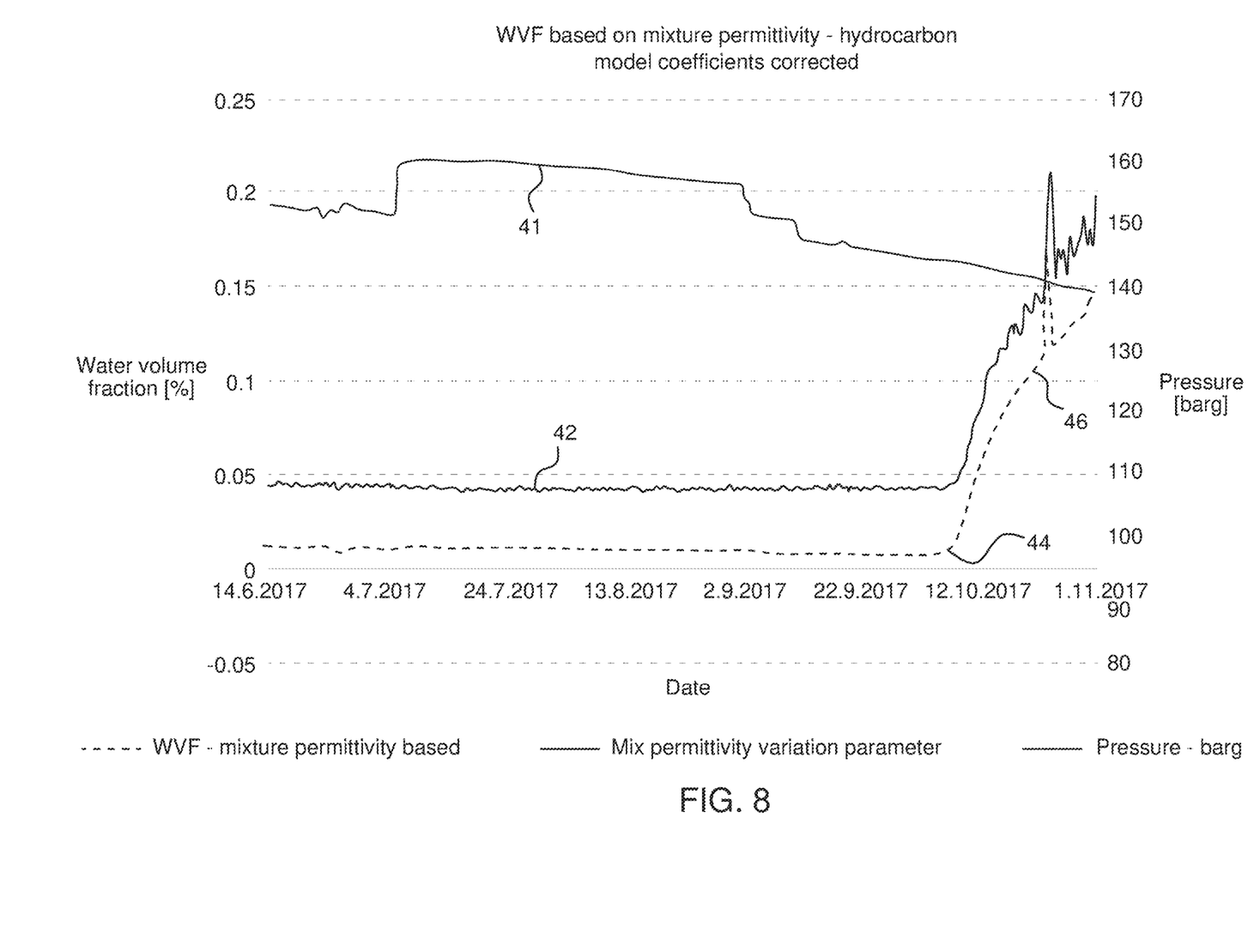
FIG. 8 shows the same real field example as in FIG. 7, where the WVF 46 is the result after correcting the detected inaccurate hydrocarbon permittivity model coefficients.

FIG. 8 is shows the same data as FIG. 7, but the WVF 46 has been post-processed in the whole period with corrected hydrocarbon permittivity coefficients found by iteration 33, as described for FIG. 4. Thus the present invention may be operated both in real time and on prestored data that can be corrected and adjusted by other measurements.

Figure 9:
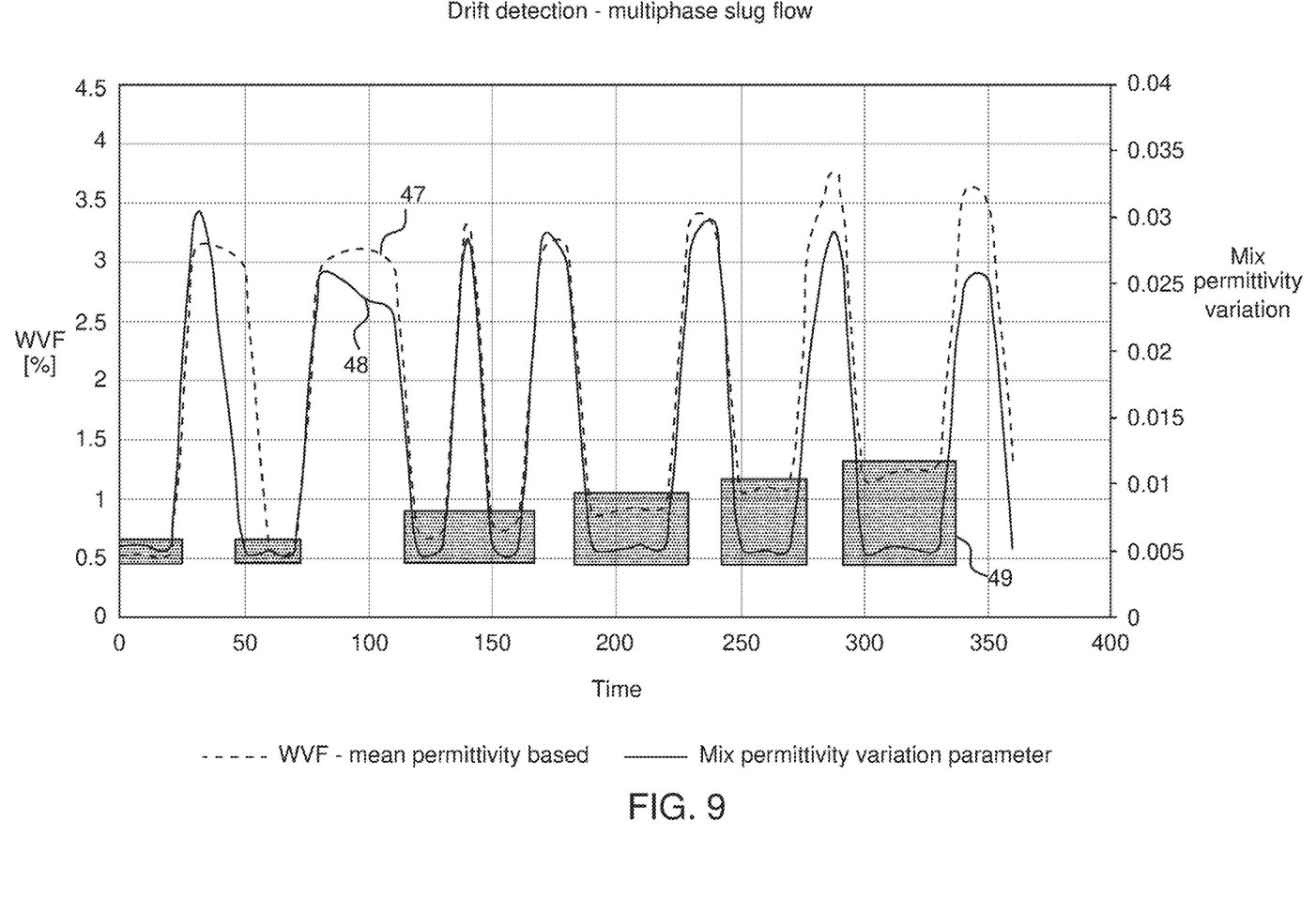
FIG. 9 shows an example of a sluggish multiphase flow where drifting of the measured water volume fraction can be detected based on evaluating the trend in the periods with low and stable mixture permittivity variation between the slugs.

FIG. 9 illustrates an example of how the invention can be used in more dynamic flow conditions. By detecting repetitive periods where the mixture permittivity variation parameter 48 is at the same level 49, one can evaluate the trending of the measured WVF 47, based on the mixture permittivity. In this example the WVF 47 is increasing in the gas rich periods between liquid slugs 49, whilst in the same periods the mixture permittivity variation 48 stays at the same level. This indicates some form of drift; it could for instance indicate the build-up of a wax or scale layer. A full characterization process, as exemplified in FIG. 4, may be run to identify potential correlations, or not, to various flow condition parameters.

The present invention may in many cases not only be able to detect drift as indicated in FIG. 3 26, but also be able to characterize the source of the drift by evaluating the trend of the said WVF and permittivity variation against the trend of other sensor inputs during the period where drift has occurred. The general prerequisite for detectable drift is a long-term trend in the measured WVF, which is not reflected by a permittivity variation trend in the same direction, see FIG. 3. The type of drift can be divided in three main categories:

Hydrocarbon permittivity model inaccuracies, see Equation 2:
  Gas permittivity: When the pressure or temperature changes, the density of the gas changes and therefor also the gas permittivity. If the calculated gas permittivity is inaccurate it will affect the WVF coming out of the mixing equation, e.g. Equation 2. The source of an inaccurate gas permittivity may be an inaccurate hydrocarbon composition, inaccurate gas permittivity model, drifting pressure, temperature or mix density sensors. FIG. 7 gives an example of the consequence of an inaccurate gas permittivity model.
  Oil permittivity: For oil dominated hydrocarbon streams the oil permittivity dominates the measured mixture permittivity. If the oil permittivity model is inaccurate it may drift with a change in temperature or pressure and affect the WVF coming out of the mixing equation, Equation 2.
  CGR: Inaccurate prediction or measurement of the split between condensate or oil and the gas, either from an Equation of State prediction model or a gamma densitometer to determine the mix density and thereof the liquid volume fraction, will give an error in the total permittivity contribution from the hydrocarbons. Oil and condensate has a higher permittivity than gas and getting the wrong split between them will cause an error in the WVF coming out of the mixing equation, Equation 2.

Affected measurement cavity, in the case of measuring the permittivity using a microwave cavity resonator. The measured resonant frequency is a function of the mechanical design of the measurement cavity, the probe design and the permittivity of the materials and fluids in the measurement cavity; consequently, any geometrical changes to the measurement cavity, or the presence of anything else than gas, oil and water will affect the derived mixture permittivity. Forms of drift that can be put into this category may be:

Various form of layers, e.g. waxing and scale. The consequence of a layer build-up on the wall in gas or oil dominating hydrocarbon flow depends on the permittivity of the layer. The permittivity of the layer is normally higher than that of the gas and will cause an over-estimation of the WVF in the wet gas flow.

Erosion changing the mechanical structure of the cavity or probes.

Corrosion changing both the mechanical structure and the metal properties.

Geometrical deformations from impacts of objects hitting the sensor cavity.

Electronic drift. All forms of mixture permittivity measurements rely on sensing the effect the medium has on an electric or electromagnetic signal. If the electronics or electromagnetic signal source itself is drifting it will affect the measured mixture permittivity and thereof the WVF in various degrees, depending on the sensor technology used. Some examples are:

Signal level drift
Signal phase drift
Signal frequency drift
Signal source impedance drift
Signal load impedance drift
Gamma densitometer drift The characterization of the source of the drift depends on the type of permittivity sensor used, but may involve the following evaluation:

Hydrocarbon model inaccuracies can be detected by analysing the WVF trend and permittivity variation trend in a predefined period, to see if there are any positive or negative correlation to the development of pressure and temperature in the same period. As can be seen in FIG. 7, the correlation between the WVF trend 43 and the pressure trend 41 is strong, which is a strong indication that the hydrocarbon permittivity model is inaccurate. The flow meter itself may use this period to post process the WVF for the whole period, with all the raw data present in the database, and self-adjust the hydrocarbon model until the measured WVF based on the mixture permittivity has the flat trend as the permittivity variation parameter indicates that it should have had.

Some of the sources of affected measurement cavity may in many cases be possible to characterise:

Any form of layer build-up or erosion of material will eventually cause a trend both in the dP reading and the WVF measurement.

Corrosion or other metal surface reactions may for resonators cause a coinciding trend in the measured Q-factor since the Q-factor relies on the conductivity of the metal surface of the resonance chamber.

While drift related to hydrocarbon permittivity inaccuracies and measurement cavity changes often can be characterized by detecting a correlation with a trend of some of the other sensor inputs, electronics drift can in many cases be characterized because the effect does not correlate with changes of any of the other sensor outputs.

The characterization methods above are examples of various embodiments of the invention using some form of pattern recognition.

To summarize the present invention relates to a system and related method utilized by the system for measuring the water volume fraction (WVF) of a mixed fluid flow in a pipe, especially wet and dry gas hydrocarbon fluid flows. The system comprising a measuring unit for measuring the dielectric permittivity of said fluid mixture, a computing unit for calculating and storing both the WVF, based on the dielectric permittivity, and the statistical variation of the dielectric permittivity of said fluid mixture over a predetermined period of time. It should be noted that permittivity in this case also relates to the complex permittivity and includes both information about static permittivity and conductivity.

The system also includes an analysis unit for detecting drift in the calculated WVF by comparing and analyzing the development of the calculated WVF versus the statistical variation of the permittivity over said time period. Based on the on detected drift it is determined if the development in the calculated WVF is reflected in a corresponding change in the statistical variation of the permittivity. The comparison and analysis will provide a means to determine if the drift is caused by a real change in the WVF or if it may have other causes, based on a list of possible explanations to the measured and calculated variations.

The WVF may be derived from the measured permittivity of the mixture, an estimated permittivity of the hydrocarbon fluid, an estimated split between oil and gas based on the hydrocarbon composition, together with some form of known mixing equations. The density of the mixture, e.g. measured using a gamma densitometer, may be added as an additional input to the equations to calculate the split between oil and gas instead of an estimation of the same based on the hydrocarbon composition.

The mixture permittivity and permittivity variation may be derived from several different measurements, for example from at least one of the measured resonance frequency and the Q-factor of a microwave resonator present in the flow or the mixture permittivity and permittivity variation may be derived from a microwave transmission sensor. It is also possible to derive the mixture permittivity and permittivity variation from a capacitive permittivity sensor, an inductive sensor or from a conductivity sensor, i.e. measuring the mixture conductivity, where the imaginary part of the mixture permittivity and the variation of the imaginary part may be measured with a conductivity sensor that is measuring the mixture conductivity and the variation of the variation of the conductivity. Other alternatives are represented by measuring the mixture permittivity and permittivity variation are derived from the power and phase shift of a microwave transmission sensor using minimum one transmitter antenna and minimum one receiving antenna or from measuring the phase and power shift of reflections of a microwave open-ended coaxial probe sensor.

The mixture permittivity and permittivity variation measurement may be performed in a measurement cavity constituted by the whole cross section of the pipe, a partial section of the pipe, e.g. on the wall, in a bend or in the blind Tee of a pipe arrangement. The measurement cavity for the mixture permittivity and permittivity variation is a custom made mechanically defined cavity, either inside or outside of the pipe, where a sample of the fluids can flow through.

If mixture conductivity and conductivity variation are used they may be derived from measuring the phase and power shift of reflections of a microwave open-ended coaxial probe sensor.

If the water content dominates the flow an increasing permittivity variation trend may be interpreted as corresponding to an increasing fraction of hydrocarbons, e.g. a watercut or multiphase meter in water-continuous flow.

The system according to the invention may include a computer storage for storing said measured permittivity, in which case the computing unit and analyzing unit may be adapted to calculate, store, compare and analyze the development in data sets stored in said computer storage, thus determining drift in a prestored data set after the measurements and not in real time.

The invention claimed is:

1. A system for measuring a water volume fraction (WVF) of a mixed fluid flow in a pipe, the system comprising:
    at least one sensor configured to measure dielectric permittivity of the fluid mixture;
    a processing unit for calculating and storing both the WVF based on the dielectric permittivity and a statistical variation of the dielectric permittivity of the fluid mixture over a predetermined period of time;
    wherein the processing unit includes a drift detection and characterization unit for detecting drift in the calculated WVF by comparing and analyzing development of the calculated WVF versus the statistical variation of the dielectric permittivity over the predetermined time period, and based on detected drift to determine whether the development in the calculated WVF is reflected in a corresponding change in the statistical variation of the dielectric permittivity; and
    wherein, based on the comparison and analysis, the processing unit determines if the drift is caused by a real change in the WVF.

2. The system according to claim 1, wherein the processing unit is configured to derive the WVF from the measured dielectric permittivity of the fluid mixture, an estimated permittivity of a hydrocarbon fluid, an estimated split between oil and gas based on a hydrocarbon composition, together with known mixing equations.

3. The system according to claim 2, wherein the processing unit is configured to add density of the fluid mixture as an additional input to the equations to calculate the split between oil and gas instead of an estimation based on the hydrocarbon composition.

4. The system according to claim 1, comprising a microwave resonator configured to measure the mixture permittivity and permittivity variation with a resonance frequency and Q-factor of at least one of the existing resonances of the microwave resonator.

5. The system according to claim 1, comprising a microwave transmission sensor configured to measure the mixture permittivity and permittivity variation.

6. The system according to claim 1, comprising a capacitive permittivity sensor configured to measure the mixture permittivity and permittivity variation.

7. The system according to claim 1, comprising an inductive sensor configured to measure the mixture permittivity and permittivity variation.

8. The system according to claim 1, comprising a conductivity sensor configured to measure an imaginary part of the mixture permittivity and the variation of the imaginary part and configured to measure the mixture conductivity and the variation of the conductivity.

9. The system according to claim 1, comprising a microwave transmission sensor comprising at least one transmitter antenna and at least one receiving antenna, and configured to measure the mixture permittivity and permittivity variation as power and phase shift of the microwave transmission sensor.

10. The system according to claim 1, comprising a microwave open-ended coaxial probe sensor configured to measure the mixture permittivity and permittivity variation as phase and power shift of reflections of the microwave open-ended coaxial probe sensor.

11. The system according to claim 1, comprising a measurement cavity comprising a whole cross-section of the pipe, the measurement cavity being configured to measure the mixture permittivity and permittivity variation.

12. The system according to claim 1, comprising a measurement cavity comprising a whole cross section of the pipe, the measurement cavity comprising a partial section of the pipe, the measurement cavity being configured to measure the mixture permittivity and permittivity variation therein.

13. The system according to claim 1, comprising a measurement cavity, wherein the measurement cavity is a custom made mechanically defined cavity as part of the pipe, wherein a sample of the fluids can flow through, the measurement cavity being configured to measure mixture permittivity and permittivity variation.

14. The system according to claim 1, wherein:
    the processing unit includes a computer storage for storing the measured permittivity; and
    the drift detection and characterization unit is adapted to calculate, store, compare and analyze the development in data sets stored in the computer storage to determine drift in a prestored data set.

15. The system according to claim 1, wherein the mixed fluid flow comprises at least one of wet and dry gas hydrocarbon fluid flows.

16. A method for measuring a water volume fraction (WVF) of a mixed fluid flow in a pipe, the method utilizing at least one sensor for measuring dielectric permittivity of the fluid mixture, the method comprising:
    calculating and storing both the WVF based on dielectric permittivity and a statistical variation of the dielectric permittivity of the fluid mixture over a predetermined period of time;
    detecting, from an analysis of the WVF, drift in the calculated WVF by comparing and analyzing development of the calculated WVF versus a statistical variation of the permittivity over the predetermined period of time;
    determining, based on the detected drift, whether the development in the calculated WVF is reflected in a corresponding change in the statistical variation of the permittivity; and
    determining, based on the comparison and analysis, whether the drift is caused by a real change in the WVF.

17. The method according to claim 16, wherein the WVF is derived from the measured dielectric permittivity of the mixture, an estimated permittivity of a hydrocarbon fluid, an estimated split between oil and gas based on a hydrocarbon composition, together with known mixing equations.

18. The method according to claim 17, wherein the density of the mixture is added as an additional input to the equations to calculate the split between oil and gas instead of an estimation based on the hydrocarbon composition.

19. The method according to claim 16, wherein the mixture permittivity and the variation of the mixture permittivity are measured by measuring phase and power shift of reflections of a microwave open-ended coaxial probe sensor.

20. The method according to claim 16, wherein the mixed fluid flow comprises at least one of wet and dry gas hydrocarbon fluid flows.

\* \* \* \* \*